(12) United States Patent
Masliah et al.

(10) Patent No.: US 7,226,746 B1
(45) Date of Patent: Jun. 5, 2007

(54) METHOD FOR SCREENING FOR ANTI-AMYLOIDOGENIC PROPERTIES AND METHOD FOR TREATMENT OF NEURODEGENERATIVE DISEASE

(75) Inventors: Eliezer Masliah, San Diego, CA (US); Makoto Hashimoto, La Jolla, CA (US); Edward Rockenstein, Chula Vista, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/806,842

(22) PCT Filed: Oct. 6, 1999

(86) PCT No.: PCT/US99/23134

§ 371 (c)(1),
(2), (4) Date: Dec. 27, 2001

(87) PCT Pub. No.: WO00/20020

PCT Pub. Date: Apr. 13, 2000

Related U.S. Application Data

(60) Provisional application No. 60/103,310, filed on Oct. 6, 1998.

(51) Int. Cl.
*G01N 33/53* (2006.01)
(52) U.S. Cl. ............... 435/7.1; 435/7.2; 435/7.21; 435/7.8; 435/7.9; 435/7.93; 436/501; 436/503
(58) Field of Classification Search ............... None
See application file for complete search history.

(56) References Cited

U.S. PATENT DOCUMENTS 6,184,351 B1 * 2/2001 Biere et al. ............... 530/350
6,504,080 B1    1/2003 Van Der Putten
6,780,971 B2 * 8/2004 Wolozin et al. ........... 530/329

OTHER PUBLICATIONS

Hashimoto et al., NeuroReport 10:717-721, 1999.*
Jensen et al., Biochem. J., 323:539-546, Apr. 15, 1997.*
Harris et al., Experimental Neurology, 1995, 131(2):193-202.*
Hashimoto et. al., The Journal of Biological Chemistry 274(41):28849-28852, 1999.*
Narhi et. al., The Journal of Biological Chemistry, 274(14):9843-9846, 1999.*
RG Perez and TG Hastings, Journal of Neurochemistry, 89(6):1318, 2004.*
Jenner et al (Sep. 1998;). Annals of Neurology. 44(suppl. 1), S72-S84.*
Lutz (1990). Mut. Res., 238, (abstract only).*
Korge et al (1993). Archives of Biochemistry and Biophysics. 304, 420-428.*
Bauminger et al (1999) Biochemistry. 38, 7791-7802.*
Guptasarma et al (1992). Biochemistry. 31, 4296-4303.*
Spillantini, M.G. et al. α-Synuclein in Lewy bodies. Nature. 388:839-40. 1997.

* cited by examiner

*Primary Examiner*—Janet L. Andres
*Assistant Examiner*—Steven H. Standley
(74) *Attorney, Agent, or Firm*—Morrison & Foerster LLP

(57) ABSTRACT

In methods for screening treatments for, and treatment of, neurodegenerative diseases, aggregation in neurons of NACP/α-synuclein is measured and expression of a non-amyloidogenic protein is stimulated in order to reduce the level aggregration. For purposes of screening agents for treatment of neurodegenerative disease, oxidative stress in the neuronal cells is stimulated by introducing a mixture of metal-ions and hydrogen peroxide. Examples of appropriate metals include iron, aluminum, and copper. After introduction of the agent under evaluation for stimulation of expression of non-amyloidogenic protein, the effectiveness is measured by testing for a decrease in the level of aggregation of NACP/α-synuclein. In an exemplary embodiment, the non-amyloidogenic protein is β-synuclein. The aggregation of NACP/α-synuclein is dependent upon the concentration of metal ions in the neuronal cells. In addition, the presence of chelating agents appears to modulate the build-up of NACP/α-synuclein aggregates which are responsible for synaptic and neuronal dysfunction.

8 Claims, 7 Drawing Sheets

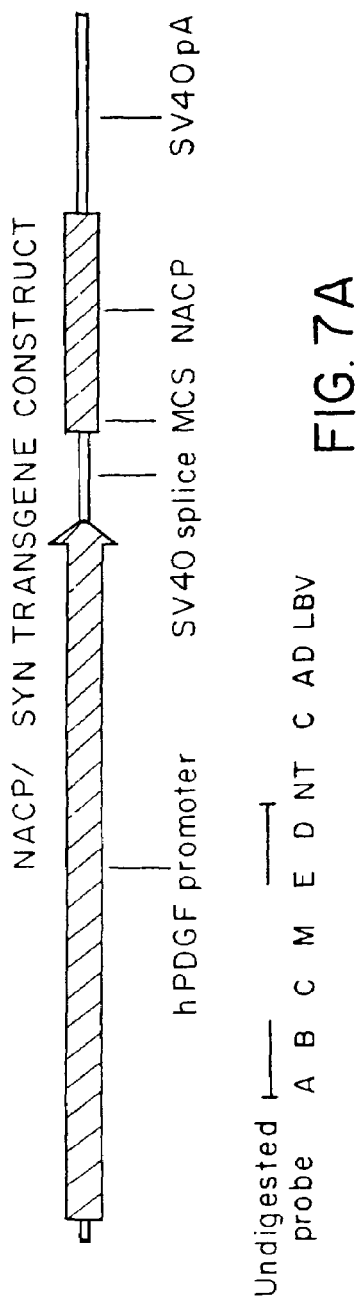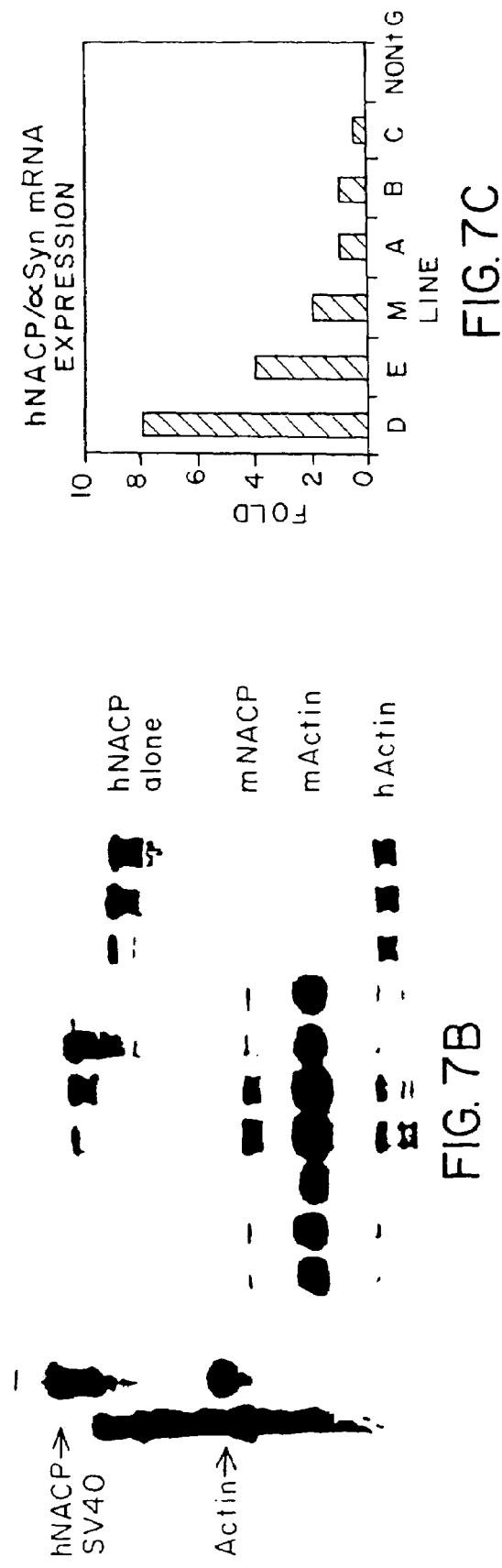

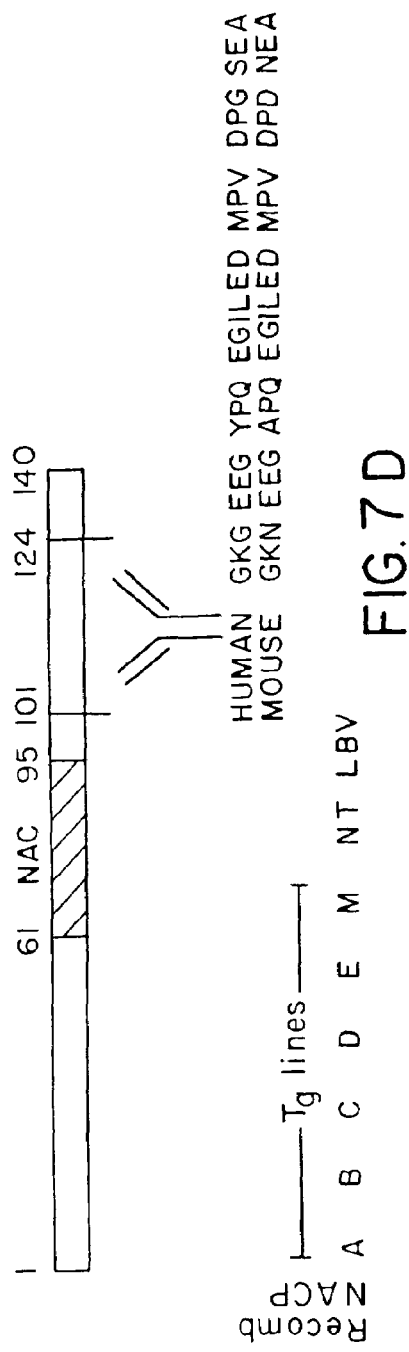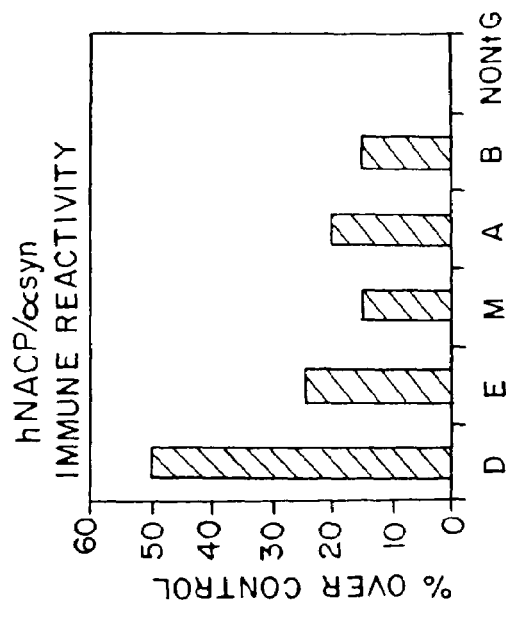
FIG. 7D
FIG. 7E
FIG. 7F

METHOD FOR SCREENING FOR ANTI-AMYLOIDOGENIC PROPERTIES AND METHOD FOR TREATMENT OF NEURODEGENERATIVE DISEASE

This application is a 371 of PCT/US9923134, filed Oct. 6, 1999, which claims benefit to provisional application 60/103,310, filed Oct. 6, 1998.

STATEMENT OF RIGHTS TO INVENTIONS MADE UNDER FEDERALLY SPONSORED RESEARCH

This work was supported in part by grants from the National Institutes of Health (NIH) by virtue of NIH grant numbers AG05131 and AG10689.

BACKGROUND OF THE INVENTION

1. Field of the Invention

This invention relates generally to the selection of inhibitors with anti-amyloidogenic activity for the treatment of neurodegenerative disease and more specifically to methods of testing and selection of inhibitory compounds with anti-amyloidogenic properties for the treatment of Parkinson's, Alzheimer's and other neurodegenerative diseases.

2. Background Information

Degenerative disorders of the central nervous system are characterized by progressive, subacute or chronic loss of neurons and their terminals accompanied by reactive alterations, including astrogliosis and microgliosis.

Some neurodegenerative disorders are determined genetically while others occur independent of genetics. In general terms, Alzheimer's disease is the most commonly occurring neurodegenerative disorder, followed by disorders associated with the presence of Lewy bodies, such as Parkinson's disease and the Lewy body variant of Alzheimer's disease.

Other less frequently occurring neurodegenerative disorders include Pick's disease, Huntington's disease, Progressive supranuclear palsy and Friedreich's ataxia, to name a few.

Neurodegenerative disorders are characterized by damage to selective neuronal populations that could be followed or preceded by synaptic injury. The mechanisms triggering cell death and synaptic damage in these disorders might be related to the increase of a toxic property and/or loss of neuroprotective capabilities of a specific neuronal cell protein. The disruption of the synaptic connections in the brain results in neuronal dysfunction that, in turn, can lead to characteristic symptoms of dementia and/or motor impairment observed in several neurodegenerative disorders.

The progressive neurodegeneration seen in Parkinson's disease exemplifies the process of synaptic and neuronal loss with concomitant plaque and tangle formation and a decrease in specific neurotransmitters. The disease is generally age related, with 66% of patients with parkinsonian symptoms being between 50 and 69 years of age.

The anatomical hallmark of Parkinson's disease is a loss in pigmentation in a region of the midbrain, known as the substantia nigra. Further, the appearance of abnormal cytoplasmic inclusions, labeled Lewy bodies, is another trademark of the disease. The substantia nigra, translated meaning "black substance", is an area of the brain rich in dopaminergic neurons and the black pigment, neuromelanin. Loss of neurons from this region in the Parkinson's disease brain leads to a dopamine deficit. The loss of cells is visibly apparent, seen as the loss of black pigment.

In addition to the loss of neuromelanin pigment in the substantia nigra, intracellular accumulations of Lewy bodies are found in many of the neurons of a Parkinson's afflicted brain. Lewy bodies are highly insoluble and difficult to characterize but may contain abnormally phosphorylated neurofilament proteins. Antibodies raised to the protein ubiquitin have been particularly useful in identifying Lewy bodies. While the role of ubiquitin in Lewy body formation is unclear, there is speculation that it may be involved in the cell's attempt to remove abnormal proteins by proteolysis. Since these proteins may be somewhat resistant to proteolysis, the build-up of these proteins leads to the inclusions seen around the neuronal cells.

Emerging evidence from genetic, neuropathological and biochemical studies points to the critical roll non-amyloid β component (NACP)/α-synuclein plays in the amyloidogenesis seen in a number of neurodegenerative diseases. NACP/α-synuclein was previously identified as a precursor of non-A β component (NAC) of Alzheimer's disease amyloid, which was co-purified with A β from the Alzheimer's disease brain. Mutations within the precursor NACP/α-synuclein of Alzheimer's disease amyloid have recently been linked to familial Parkinson's disease and this molecule has been found to be a major component of Lewy bodies. This would suggest that abnormal accumulations of NACP/α-synuclein might play a role in the pathogenesis of disorders with Lewy bodies. Research by Spillantini, et al. (*Nature*, 388: 839–40, 1997), Takeda, et al. (*Am. J. Pathol.*, 152: 367–72, 1998) and Baba, et al. (*Am. J. Pathol.*, 152: 879–84, 1998) subsequently showed that neuronal inclusion Lewy bodies and positive neurites, observed in both sporadic Parkinson's disease and dementia with Lewy bodies disease, were strongly immunoreactive with anti-NACP/α-synuclein antibodies, and recognized both the – and C-terminals of the protein. This would indicate that NACP/α-synuclein is aggregated as a full length molecule into Lewy bodies.

A central question raised by many of these experimental findings concerns the molecular mechanism by which NACP/α-synuclein is aggregated under pathological conditions. Previous biochemical studies in vitro have shown that the aggregation of NACP/α-synuclein was stimulated by a number of amyloidogenic peptides and by specific metals, including aluminum and iron. In addition, NACP/α-synuclein was shown to bind phospholipids, causing a dramatic increase in the α-helicity of it's structure which may, in fact, be a prerequisite for the inhibition of aggregation of NACP/α-synuclein.

While it is understood that the aggregation of NACP/α-synuclein may play a critical role in the pathogenesis of Parkinson's and Lewy body disease the exact mechanism of this process remains unclear. As such, it is important to determine which factors promote abnormal aggregation and fibrillogenesis of this molecule if an effective treatment is ever to be found. The cause of selective degeneration of melanized dopaminergic neurons in the substantia nigra of the Parkinson's brain also remains unsolved. While there is speculation that the excessive production of free radicals during dopamine auto-oxidation into neuromelanin may account for cell cytotoxicity, what makes some neurons more susceptible to damage than others is not completely understood.

Thus, the need remains for a method that will allow for the elucidation of the amyloidogenic process seen in neurodegenerative diseases, such as Parkinson's and Alzheimer's disease, as well as a means for the testing and selection of therapeutic agents that have potential anti-amyloidogenic characteristics. The present invention satisfies these needs and provides related advantages as well.

SUMMARY OF THE INVENTION

It is an advantage of the present invention to provide a means for testing the role NACP/α-synuclein plays in the aggregation of Lewy bodies, seen in a number of neurodegenerative diseases, in response to reactions involving oxidative stress within the neuronal cells of the substantia nigra region of the brain.

It is another advantage of the present invention to further provide methods for the screening and evaluation of anti-amyloidogenic properties through the manipulation of expression of non-amyloidogenic proteins.

It is still another advantage of the present invention to provide a method to examine the role of the abnormal accumulation of NACP/α-synuclein, as a result of NACP/α-synuclein protein overexpression, plays in neuropathological alterations similar to that seen in Lewy body disease.

In an exemplary embodiment of the present invention, aggregation in neurons of NACP/α-synuclein is measured and expression of a non-amyloidogenic protein is stimulated in order to reduce the level aggregation. For purposes of screening agents for treatment of neurodegenerative disease, oxidative stress in the neuronal cells is stimulated by introducing a mixture of metal-ions and hydrogen peroxide. Examples of appropriate metals include iron, aluminum, and copper. After introduction of the agent under evaluation for stimulation of expression of non-amyloidogenic protein, the effectiveness is measured by testing for a decrease in the level of aggregation of NACP/α-synuclein. In an exemplary embodiment, the non-amyloidogenic protein is β-synuclein. The aggregation of NACP/α-synuclein is dependent upon the concentration of metal ions in the neuronal cells. In addition, the presence of chelating agents appears to modulate the build-up of NACP/α-synuclein aggregates which are responsible for synaptic and neuronal dysfunction.

BRIEF DESCRIPTION OF THE DRAWINGS

FIG. 1a shows relative levels aggregation of NACP/α-synuclein with ferric ion concentration; FIG. 1b shows effects of treatment of samples with deferoxamine; and FIG. 1c compares recombinant β-synuclein and NACP/α-synuclein 112 proteins treated with ferric ion.

FIG. 2a shows the chemical reaction for iron-catalyzed oxidation and its effect on aggregation of NACP/α-synuclein; and FIG. 2b illustrates the results of an immunoblot analysis of NACP/α-synuclein aggregation with hydrogen peroxide concentration.

FIG. 6b provides a histogram of the ratio of aggregation versus monomer.

FIGS. 7a–f illustrate the characterization of NACP/α-synuclein expression in human α-synuclein transgenic mice, where FIG. 7a provides the construct of the human PDGFβ promoter driven encoding human α-synuclein; FIG. 7b shows α-synuclein mRNA levels in brain tissues from non-transgenic and transgenic mice and from humans with neurological disease; FIG. 7c illustrates a bar graph of the PhosphorImager analysis of human α-synuclein mRNA expressed as a percentage of the human control; FIG. 7d illustrates a comparison of human (Seq ID 15) and murine (Seq ID 16) NACP/α-synuclein sequences; FIG. 7e shows the Western blot analysis showing affinity-purified human- and mouse-specific α-synuclein antibodies; and FIG. 7f shows the PhosphorImager analysis of human α-synuclein signals from semi-quantitative Western blots of human α-synuclein expression in the different transgenic lines.

DETAILED DESCRIPTION OF THE PREFERRED EMBODIMENT

Figure 1A:
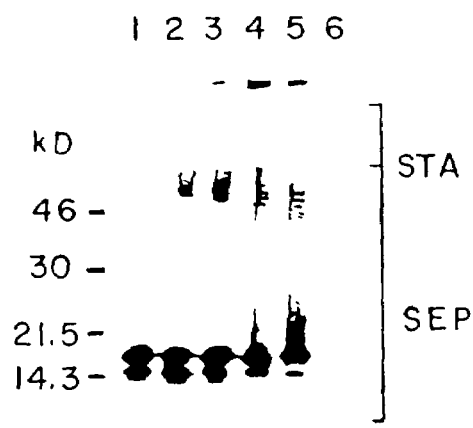
FIGS. 1a–1c illustrate the results of immunoblot analyses of the aggregation of NACP/α-synuclein by ferric ion, where

The present invention provides a means to test the role NACP/α-synuclein plays in the aggregation of Lewy bodies, seen in a number of neurodegenerative diseases, in response to reactions involving oxidative stress within the neuronal cells. The precursor of the non-amyloid β protein (Aβ) component (NAC) of Alzheimer's disease amyloid NACP (α-synuclein) is a presynaptic protein composed of 140 amino acids. NACP belongs to an expanding synuclein superfamily of peptides that includes α-synuclein (a NACP homologue), β-synuclein, γ-synuclein. While the exact function of this family remains unclear, there is a relation to certain synaptic functions known to be involved in neural plasticity, synaptic formation and neuronal development. NACP/α-synuclein is encoded by a gene in chromosome 4, which encodes full length NACP/α-synuclein 140 and an alternatively spliced shorter and rare variant denominated NACP/α-synuclein 112.

Recent genetic studies by Polymeropoulos, et al. (Science, 276: 2045–47, 1997) and Kruger, et al. (Nature Genet., 18: 106–08, 1998) have revealed that missense mutations in NACP/α-synuclein are linked to two familial types of Parkinson's disease. These mutations include an Ala53Thr substitution and an Ala30Pro substitution, both of which are autosomal-dominant, providing evidence that a possible toxic gain of function of NACP/α-synuclein might be responsible for each case of Parkinson's disease. Because the phenotypes of these familial types of Parkinson's disease were clinically and pathologically within the similar spectrum of sporadic Parkinson's disease, it was predicted that NACP/α-synuclein may also play an important role in the sporadic form of the disease. Consistent with these findings, it has been shown that Lewy bodies and ubiquitin-positive neurites observed in both idiopathic Parkinson's disease and in Lewy body disease were strongly immuno-reactive with anti-NACP/α-synuclein antibodies and that Lewy bodies contain fragments and aggregates of NACP/α-synuclein. Because it is surmised that the aggregation of NACP/α-synuclein may play a critical role in the pathogenesis of Parkinson's disease, it is important to determine which factors promote abnormal aggregation and fibrillogenesis of the molecule. In response, a study by Hashimoto, et al. (Brain Res., 799: 301–06, 1998) has shown that human recombinant NACP/α-synuclein was preferentially aggregated under certain conditions, such as low pH, time lag, and high temperature. Aluminum salts also promoted NACP/α-synuclein aggregation. Electron microscopic and histochemical studies revealed that these in vitro aggregates formed Thioflavine-S positive filaments, reminiscent of amyloid fibrils. Lewy bodies in the Parkinson's disease brain have shown that mild Thioflavine-S reactivity and NACP/α-synuclein is an important component of Lewy body fibrils. Thus, systems using recombinant NACP/α-synuclein appeared to provide a possible explanation of the mechanisms of NACP/α-synuclein aggregation.

Iron is found in abundance in the substantia nigra and its increase, as seen in Parkinson's disease, has been reported. It has been hypothesized that aberrant iron metabolism might be involved in the process of NACP/α-synuclein aggregation, and that in the presence of hydrogen peroxide ($H_2O_2$), the ferric ion stimulates in vitro aggregation which displays amyloid-like properties and are Thioflavine-S positive.

Through the elucidation of the mechanisms found in free radical production and the formation of aggregates of NACP/α-synuclein in the Parkinson's brain, the present invention provides a means for the testing and selection of therapeutic agents designed to interrupt the formation of these aggregates, thus halting the progression of the disease.

Preparation of Recombinant Protein Variations of NACP/α-Synuclein

Human recombinant NACP/α-synuclein 140, β-synuclein and NACP/α-synuclein 112 are produced using the PROEX-1 6xHis expression system (GIBCO-BRL, Grand Island, N.Y.) by the following method. The PROEX-1 expression vector containing either NACP/α-synuclein 140, β-synuclein or NACP/α-synuclein 112 as an insert is transfected to DH5α, followed by induction with IPTG. The cells are harvested and re-suspended in 50 mM Tris-HCl, pH 8.5, containing protease inhibitors. Following sonication and centrifugation of the re-suspension, the supernatant is applied to a Ni-NTA column and eluted with 20 mM Tris-HCl, pH 8.5, containing 100 mM KCl, 100 mM imidazole, 10 mM v/v glycerol and 10 mM β-mercaptoethanol. The eluted fusion protein is dialyzed against 50 mM Tris-HCl, pH 8.5, cleaved with recombinant TEV protease and again applied to a Ni-NTA column. The recombinant NACP/α-synuclein is isolated in the flow through fractions, pooled and stored at −20° C. until use.

Immunoblotting Analysis Using Anti-C-Terminal Rabbit Polyclonal Antibody

Prior to experimentation, each of the recombinant proteins need to be desalted by way of passage through PD 10 columns (Pharmacia, Piscataway, N.J.) in water and then adjusted to a final concentration of 5 μM. NACP/α-synuclein protein (1 μl) is incubated in a total volume of 20 μl of buffer containing 20 mM Tris-HCl, pH 7.4. To perform the immuno-blotting analysis, each sample is resolved by SDS-PAGE (15%) and blotted onto nitrocellulose membrane (Schleicher & Schuell, Keene, N.H.). The blotted membrane is blocked with Tris-Buffered saline (TBS; 20 mM Tris-HCl, pH 7.5 and 150 mM NaCl) containing 3% BSA, followed by incubation with anti-C-terminal rabbit polyclonal antibody (1:1000) in TBS containing 1% BSA. The blocked membrane is then incubated with peroxidase-labeled anti-rabbit IgG (Amersham) (1:1000) and visualized using the ECL immuno-blotting system (Amersham, Cleveland, Ohio), the use of which is well known to those in the art.

Histochemical Analysis of Iron-Induced NACP/α-Synuclein Aggregates

In order to determine if iron-induced NACP/α-synuclein aggregates display amyloid-like characteristics, Thioflavine-S staining is performed. 10 μl NACP/α-synuclein (140 or 112) or 10 μl β-synuclein aliquots, prepared as above, are pipetted onto glass slides, stained with Thioflavine-S, and then analyzed using a laser scanning confocal microscope.

The present invention also provides a method to examine the role the abnormal accumulation of NACP/α-synuclein, as a result of NACP/αsynuclein protein overexpression, plays in the pathological alterations similar to that seen in Lewy body disease.

Histological analysis of neuronal inclusion Lewy bodies and ubiquitin-positive neurites found in both sporadic Parkinson's disease and dementia with Lewy body disease are strongly immunoreactive with anti-NACP/α-synuclein antibodies which recognize both the − and C-terminals of the protein, which indicates that the full length NACP/α-synuclein molecule is involved in Lewy body aggregation. Additional biochemical analysis in vitro indicate that the aggregation of NACP/α-synuclein is stimulated by amyloidogenic peptides, such as Aβ and NAC, and by specific metals, including aluminum and iron. Further, NACP/α-synuclein is shown to bind to phospholipids. The resulting dramatic increase in the α-helicity of its structure indicates that the binding of NACP/α-synuclein to specific lipids bound to membrane/vesicles is a prerequisite for the inhibition of aggregation of NACP/α-synuclein.

In the native form, the protein structure of NACP/α-synuclein is in an unfolded and elongated confirmation, allowing for easy interaction with various cytoplasmic proteins. Additionally, NACP/α-synuclein readily forms a heterodimer with the closely related β-synuclein molecule, and in the absence of additional molecules, NACP/α-synuclein forms a homodimer with itself.

Based on the ability of β-synuclein to form a heterodimer with NACP/α-synuclein, as opposed to the homodimer, it is probable that β-synuclein exhibits some kind of modulatory effect on the aggregation of NACP/α-synuclein. In studies by Nakajo (*J. Neurochem.*, 55: 2031–38, 1990), Jakes, et al. (*FEBS Lett.*, 345: 27–32, 1994) and Spillantini, et al., *Proc. Nat'l Acad. Sci.*, 95:6469–73, 1998), it has been shown that β-synuclein may not be amyloidogenic in vivo and that there is an absence of immunoreactivity in Lewy bodies, which is due to the incomplete NAC domain of β-synuclein, one of the main differences between NACP/α-synuclein and β-synuclein.

Through the characterization of the amyloidogenic properties of β-synuclein and its mutants, and the elucidation of the association of β-synuclein with NACP/α-synuclein, the present invention provides a strategy for the testing and selection of therapeutic agents designed to negatively regulate the aggregation of NACP/α-synuclein in vitro through the manipulation of expression of non-amyloidogenic proteins.

Plasmid Construction and Preparation of Recombinant Proteins

Human NACP/α-synuclein, human β-synuclein, and its mutants, β-synuclein δ1 and β-synuclein δ6, are produced using the PROEX-1 6xHis expression system (GIBCO-BRL, Grand Island, N.Y.) as previously described. The constructions of PROEX-1—NACP/α-synuclein and PROEX-1-β-synuclein are previously described (Hashimoto, et al., *Brain Res.*, 799: 301–06, 1998). PROEX-1-β-synuclein δ1 is constructed by a two-step PCR protocol as follows:

Initially, primer pairs, either a sense primer BSYNNDE, encoding amino acids 1–7 of β-synuclein (SEQ ID NO: 1) and an NdeI site at its 5' end, and an antisense primer, corresponding to amino acids 73–83 of α-synuclein and amino acids 66–72 of β-synuclein (SEQ ID NO: 2), or a sense primer, corresponding to amino acids 73–83 of α-synuclein and amino acids 73–79 of β-synuclein (SEQ ID NO: 3) and an antisense primer BSYNNOT encoding amino acids 129–134 of β-synuclein and NotI site at its 5' end (SEQ ID NO: 4) are incubated in PCR with plasmid pCEP4-human β-synuclein as a template. Individual PCR products are gel-purified and an aliquot of each product is combed with primers BSYNNDE (SEQ ID NO: 1) and BSYNNOT (SEQ ID NO: 4) to synthesize a full length of β-synuclein δ1 cDNA. The resulting PCR product is digested with NdeI and NotI and ligated to PROEX-1 previously digested with NdeI and NotI, finally to produce PROEX-1-β-synuclein δ1.

PROEX-1-β-synuclein δ2 is similarly constructed by a two-step PCR protocol using PROEX-1-β-synuclein δ1 as a template. Initial primer pairs are either BSYNNDE (SEQ ID NO: 1) and an antisense primer corresponding to amino acids 55–62 of β-synuclein and amino acids 63–72 of α-synuclein (SEQ ID NO: 5) or a sense primer encoding amino acids 63–79 of α-synuclein (SEQ ID NO: 6), and BSYNNOT (SEQ ID NO: 4). For both of the newly-constructed plasmids, fidelity of the sequencing is confirmed using a commercially available delta taq cycle sequencing kit (Amersham).

In order to test the susceptibility of the newly constructed β-synuclein mutants to aggregation, an aggregation assay can be performed. To do this, 10–20 μM of each of the mutant proteins are incubated in a total volume of 20 μl with a final concentration of 100 mM sodium acetate, pH 6.9. Aggregation can be induced under a variety of conditions, for instance, low pH and high temperature. SDS-PAGE analysis/immunoblotting or Thioflavine-S staining provides means for evaluating the reacted samples, the methods of which are described above and well known to those in the art.

Histochemical Analysis of β-Synuclein Mutants

In order to determine whether the aggregates resulting from aggregation reactions of PROEX-1-β-synuclein δ1 and PROEX-1-β-synuclein δ2 display amyloid-like characteristics, 10 μl aliquots of the protein preparations are obtained using the above-described procedures are pipetted onto glass slides and stained with Thioflavine-S. The results are visually analyzed using a confocal microscope, the method of which is well known to those in the art.

In Vitro Binding Assay

Samples containing 0–20 μM of NACP/α-synuclein are incubated at 37° C. for 8 hours in combination with or without His-tagged β-synuclein (20 μM) in a total volume of 20 μl at pH 6.9. At the completion of the first incubation period, $Ni^{2+}$ beads, equilibrated with buffer A (20 mM Tris-HCl, pH 8.5, 100 mM KCl, 2 mM imidazole, 10 mM 2-mercaptoethanol and 10% glycerol), are added to the samples and left to sit for one hour at 4° C. Following recovery of the beads by pulse centrifugation, the beads are washed three times with buffer A, once with buffer B (20 mM Tris-HCl, pH 8.5, 100 mM KCl, 20 mM imidazole, 10 mM 2-mercaptoethanol and 10% glycerol), and once again with buffer A. The beads are then boiled in SDS sample buffer, and subjected to 15% SDS-PAGE. NACP/α-synuclein is then visualized by the immunoblotting analysis described below.

Immunoblotting Analysis Using Anti-NACP101–124 Polyclonal Antibody

NACP/α-synuclein-specific polyclonal antibody (anti-NACP101–124) is raised against the synthetic peptide 'GKGEEGYPDEGILEDMPVDPGSEA' (SEQ ID NO: 9) which is derived from residues 101–124 of NACP/α-synuclein. Immunoblotting analysis is performed as described above, the method of which is well known to those in the art. Briefly, each sample is resolved by SDS-PAGE (15%) and blotted onto nitrocellulose membrane (Schleicher & Schuell, Keene, N.H.) using a standard transfer apparatus. The membrane is then blocked with TBS containing 3% BSA, followed by an incubation with anti-NACP101–124 (1:1000) in TBS containing 1% BSA. The treated membrane is then incubated with $^{125}$I-labeled protein A (ICN, Costa Mesa, Calif.), followed by autoradiography.

The present invention also provides a method for examining the impact of abnormal accumulation of NACP/α-synuclein, resulting from wild type α-synuclein protein overexpression, on neuropathological alterations similar to those seen in Lewy body disease.

In order to better understand if the accumulation of α-synuclein results in neurodegenerative alterations similar to Lewy body disease, a line of transgenic mice were created in which wild type human α-synuclein is over-expressed under the regulatory control of the platelet-derived growth factor β (PDGFβ) promoter. The transgenic mice were generated using the procedure described below. The PDGFβ promoter was chosen because it has been used successfully to target the expression of other human proteins to neurons in transgenic models of neurodegenerative disorders.

Human α-synuclein is a 140 amino-acid molecule (SEQ ID NO:10) that is encoded by a gene on chromosome 4 and was originally isolated from plaques of Alzheimer disease brains. Involved in synaptic function and neural plasticity, this 19 kD protein is a precursor of the highly hydrophobic 35 amino-acid metabolite, non-amyloid component (NAC). The NAC peptide can self-aggregate into fibrils and induces aggregation of the Aβ peptide.

Generation of Transgenic Mice

The transgene used for microinjection consists of a PDGFβ promoter, an SV40 intron, the human wild-type NACP/α-synuclein cDNA, and the SV40 poly A. FIG. 7a illustrates the construct of the human PDGFβ promoter driven encoding human α-synuclein. This transgene is constructed by first subcloning the PDGFβ promoter into the EcoRI/XhoI site of pNASSβ using an EcoRI/XbaI linker. The portion of the β-gal cDNA and poly A signal in the resulting plasmid is substituted with the Not/SalI fragment of the pCEP4-NACP/α-synuclein which encodes human wild-type NACP/α-synuclein cDNA plus SV40 poly A cDNA. The purified construct is linearized by digestion with SalI/ScaI and injected into prenuclear mouse embryos from superovulated females and re-implanted in pseudo-pregnant female B6/DBA2 mice. The offspring genotype is confirmed by slot blot, the procedure of which is well known to those in the art.

Thirteen founder mouse lines are generated and crossed with wild-type, B6/DBA2 mice. The resulting mice from each line are screened by PCR using tail DNA. Briefly, genomic DNA is extracted using a standard protocol, known to those in the art. PCR is run at 30 cycles: 93° C.×30 seconds, 57° C.×1.5 minutes, 72° C.×5 minutes; using a sense primer (SEQ ID NO: 7) and an antisense primer (SEQ ID NO: 8).

Offspring from each line are sacrificed in order to determine the levels of mRNA expression, using ribonuclease protection assay (RPA) analysis, and protein expression using Western blot and immunochemical analysis. After the initial screening and characterization, the mouse lines that show high, intermediate, and low levels of transgene expression are selected for subsequent breeding and neuropathological analysis.

Tissue Processing

Heterozygous mice from transgenic lines expressing high, intermediate and low level of NACP/α-synuclein, as well as non-transgenic littermates are perfused with cold saline and the brains removed, intact. The left hemibrain is frozen with isopentane and cooled in a Histobath (Shandon Lipshaw, Pittsburgh, Pa.) and the right hemibrain is immersion-fixed in 4% paraformaldehyde in pH 7.4 phosphate buffered saline (PBS). The frozen samples of the left hemibrain are bisected and processed for RPA, Western blot and dot blot analysis. The immersion-fixed right hemibrains are serially sectioned into 40 μm slices with the Vibratome 2000 (Leica, Deerfield, Ill.) for subsequent neuropathological, immunocytochemical/computer aided imaging and ultrastructural analysis. An additional subset of paraformaldehyde-fixed brains is paraffin-embedded and serially sectioned at 7 μm for H & E and Cresyl violet staining and in situ hybridization.

Analysis of NA CP/α-Synuclein Transgene mRNA Expression

For the RPA analysis, the human NACP/α-synuclein/SV40 riboprobe is generated by PCR using primers located in the PDGF-h NACP/α-synuclein transgene. The sense primer is a 20-mer starting at nucleotide no. 194 of h NACP/α-synuclein (GenBank Accession #L08850). The anti-sense primer is a 21-mer starting at nucleotide no. 270 of the SV40 poly A signal of pCEP4 vector (Invitrogen). This poly A signal is used to construct the PDGF-h NACP/α-synuclein transgene. The riboprobe is 420 nucleotides in length and can also recognize approximately 100 nucleotides of the murine NACP/α-synuclein. As a loading control, an actin riboprobe is used which recognizes the 79 base pair fragment (bp 480–559) of both murine and human actin mRNA fragments. An RPA is performed as previously described and blots are imaged with a PhosphorImager and the resulting data quantified using the ImageQuant software. With the ImageQuant software, NACP/α-synuclein mRNA levels are manipulated to more closely correlate with actin expression levels.

Additional analysis of the patterns of mRNA expression is done using in situ hybridization, utilizing probes that recognize endogenous murine and transgenic h NACP/α-synuclein. The probes used for the in situ hybridization are essentially the same as the ones used for the ribonuclease protection assays with the exception that the probes for the in situ hybridization are labeled with $S^{35}$, while the probes used in the ribonuclease protection assays are labeled with $P^{32}$. Briefly, as described above, paraffin sections from transgenic and non-transgenic mice are treated with proteinase K, followed by equilibration in prehybridization solution and hybridization with the sense and then the anti-sense probes, with incubations at 55° C. and 60° C. respectively. Exposure of x-ray film is allowed to proceed over a period of two weeks.

Antibodies

Immunocytochemical and Western blot studies are done using affinity-purified rabbit polyclonal antibodies raised against the N-terminal NACP/α-synuclein (aa1-9), the C-terminal NACP/α-synuclein (aa131–140) and NAC (X1, aa61–69). These antibodies are prepared by inoculating rabbits with synthetic peptides, followed by purification using affinity chromatography. Because these antibodies can not differentiate human from murine NACP/α-synuclein, additional analysis is performed using species-specific antibodies. These antibodies are generated by inoculating with rabbits with a set of peptides from the sequences spanning amino-acids 101–124 of the human and murine NACP/α-synuclein C-terminal region. Sequence analysis with the commercially available Align Plus, version 30 program (Scientific & Educational Software, Copyright 1997) reveals that this region contains only a four amino-acid difference between the human and murine NACP/α-synuclein sequences, as can be seen in the representative sequence of FIG. 7d. Double-immunolabeling studies for localization of NACP/α-synuclein in the synapses are performed with mouse monoclonal antibody raised against synaptophysin (SY38, Boehringer Mannheim, Indianapolis, Ind.). Studies of synapto-dendritic integrity are done with mouse monoclonal antibodies raised against both synaptophysin and microtubule-associated protein 2 (MAP2, Boehringer Mannheim). Studies to measure the damage to specific neuronal populations is performed with antibodies raised against calbindin (1:1000, Sigma, St. Louis, Mo.), parvalbumin (1:1000, Sigma) and tyrosine hydroxylase (1:10, Boehringer). The neuropathological analysis for the study of Lewy body and plaque formation are done using rabbit polyclonal antibody against ubiquitin (DAKO Corp., Carpinteria, Calif.) and biotinylated mouse antibody against amyloid-β (clone 3D6, Althena Neurosciences, San Francisco, Calif.), respectively.

Analysis of NACP/α-synuclein Transgene Protein Expression

Briefly, as previously described, blind-coded vibratome sections from transgenic and non-transgenic mice are first washed in PBS, treated with $H_2O_2$, blocked with serum and then incubated overnight at 4° C. with the antibodies against NAC and C- and N-terminal NACP. Upon completion of incubation, the sections are washed and incubated with biotinylated goat anti-rabbit IgG, followed by Avidin D-HRP (ABC Elite, Vector Laboratories, Burlingame, Calif.) and then reacted with diaminobenzidine tetrahydrochloride (DAB) containing 0.001% $H_2O_2$. Further analysis of NACP/α-synuclein immunolocalization is done by double labeling the sections with antibodies against NACP/α-synuclein and synaptophysin, as described above, followed by imaging with the laser scanning confocal microscope. Additional analysis of human and murine NACP/α-synuclein expression is done by Western blot. Briefly, as described above, brain samples are homogenized, fractionated into cytosolic and particulate components with the samples then loaded onto SDS-PAGE gels. Following a standard protocol, the gels are blotted onto nitrocellulose paper and the blots are then incubated with antibodies against C-terminal human and murine NACP/α-synuclein, followed by incubation in $^{125}$I-protein A. The resulting blot images are digitized with the PhosphorImager and the specific 19 kD bands corresponding to human and murine NACP/α-synuclein are quantified using the accompanying software.

Ultrastructural and Immunoelectron Microscopy

To further study the alterations seen in brain tissue associated with NACP/α-synuclein overexpression, vibratome sections are postfixed with 2% glutaraldehyde/0.1% osmium tetroxide in 0.1 M sodium cacodylate buffer and then embedded in epoxy resin. The resin blocks are sectioned with an Ultracut E ultramicrotome (Leica) and viewed using a Zeiss EM10 electron microscope (Carl Zeiss, Germany). An additional set of vibratome sections are post-fixed briefly in 3% paraformaldehyde in 0.1 M sodium cacodylate, pH 7.4, buffer. Tissues are washed in 0.1 M sodium cacodylate buffer containing 100 mM glycine immunolabeled with antibodies against calbindin, parvalbumin and tyrosine hydroxylase and reacted with DAB. Anti-calbindin- and parvalbumin-immunostained cells are counted in 0.1 $mm^2$ fields using a 40× objective and a gridded 10× eyepiece lens. For the frontal cortex and basal ganglia, results are expressed as immunolabeled neurons per square millimeter and for the hippocampus as the total number of calbindin-immunoreactive neurons per subdivision of the Cornus Amonis. The number of tyrosine hydroxylase-immunoreactive neurons in the substantia nigra are expressed as numbers per unit area. Further semiquantitative assessment of calbindin, parvalbumin, and tyrosine hydroxylase immunoreactivity in the neocortex, basal ganglia and hippocampus are performed using the commercially available microdensitometric system of the Quantimet 570C.

Disclosed herein is a strategy for a testing means which confirms that the conditions associated with oxidative stress preferentially promote the aggregation of NACP/α-synuclein, but not β-synuclein. Because NACP/α-synuclein 112, the splicing variant which lacks the majority of the C-terminal region of NACP/α-synuclein is aggregated, it is possible that some amino-acid sequences of the NAC domain, which are deleted in β-synuclein, are essential for the aggregation of NACP/α-synuclein by ferric ion. In addition, since iron promotes NACP/α-synuclein self aggregation, the aberrant accumulation of ferric ion is shown to be a risk factor for the aggregation of NACP/α-synuclein in the Parkinson's disease brain.

The testing method of the present invention also confirms that neuromelanin, found in the substantia nigra, acts as an endogenous chelator of ferrous/ferric ions and differentially regulates the rate of hydroxyl radical production. Oxidative stress mediated by ions such as iron is involved in the amyloidogenesis of Aβ protein, and as such, indicates that amyloid fibrils exert their toxicity, at least in part, via oxidative stress. It is believed that aggregation of NACP/α-synuclein is not only a result of increased ferric ions via oxidative reaction, but can also be a trigger/stimulator of the iron-catalyzed oxidative reactions.

These results suggest that the iron-catalyzed oxidation and aggregation of NACP/α-synuclein can be mutually synergistic. In Alzheimer's disease as well as other conditions where oxidative stress leads to aggregation of synaptic proteins with amyloidogenic potential, it is possible that this abnormally aggregated molecule can mediate the neurodegenerative process. As such, a potential target, the abnormal aggregation of NACP/α-synuclein mediated by oxidative stress, is identified for which therapeutic agents may be designed to work against.

Further disclosed herein is a strategy for testing the cell type specific factors which directly or indirectly modulate the aggregation of NACP/α-synuclein in certain areas of the brain. β-synuclein is not an amyloidogenic protein. However, β-synuclein mutants whose incomplete NAC domains are substituted with the corresponding NAC domain of NACP/α-synuclein, are transformed into amyloidogenic proteins which indicates that the NAC domain is a critical determinant in the amyloidogenic properties of synucleins. The co-incubation of β-synuclein with NACP/α-synuclein exhibits dose-dependant inhibition of the aggregation of NACP/α-synuclein in vitro, and as such, β-synuclein, a non-amyloidogenic molecule due to the incomplete NAC domain, acts as a negative regulator of the aggregation of NACP/α-synuclein.

The balance of the expression level of NACP/α-synuclein versus β-synuclein could be important for the regulation of the aggregation of NACP/α-synuclein in vivo. In this regard, the expression of NACP/α-synuclein and β-synuclein are differentially regulated, in a region specific manner in the CA3 layer of the hippocampus in the brain, and in the differentiation-stage specific manner in a megakaryocyte-platelet system. As such, the cell type specific mode of the differential gene regulation of NACP/α-synuclein and β-synuclein could be predeterminant of the aggregation of NACP/α-synuclein.

These results suggest that NACP/α-synuclein and its related molecule, β-synuclein, are amyloidogenic and non-amyloidogenic partners which interact with each other to regulate amyloidogenesis. If amyloid formation of specific amyloidogenic proteins are causative for neurodegeneration, the method of the present invention for selection of therapeutic agents designed to negatively regulate the aggregation of NACP/α-synuclein in vitro through the manipulation of expression of non-amyloidogenic proteins represents an effective therapeutic strategy.

Still further disclosed herein is a method to evaluate the role abnormal accumulation of NACP/α-synuclein plays in the neuropathological alterations seen in specific areas of the brain. The neuronal expression of human α-synuclein, in transgenic mice, results in the progressive accumulation of α-synuclein- and ubiquitin-immunoreactive inclusions in deep layers of the neocortex, the hippocampal CA3 region of the brain, the olfactory bulb and, occasionally, in the substantia nigra. Notably, these regions are typically also affected in patients with Lewy body disease.

Ultrastructural analysis reveals the presence of both electrodense intranuclear deposits and cytoplasmic inclusions in the deep layers of the neocortex and in the dopaminergic neurons in the substantia nigra of the human α-synuclein transgenic mice. Further analysis of the integrity of dopaminergic cell bodies in the substantia nigra and their nerve terminals in the striatum have lead to findings suggesting that the abnormal accumulation of human α-synuclein may lead to injury of synapses in the absence of overt neuronal loss.

The loss of dopaminergic terminals and apomorphine-responsive abnormalities in motor performance observed in human α-synuclein transgenic mice suggests that intraneuronal accumulations of amyloidogenic synaptic proteins can elicit morphological and functional central nervous system alterations. The alterations observed in human α-synuclein transgenic mice resemble alterations found in human neurodegenerative diseases with Lewy bodies.

These results suggest that the increased expression of wild type α-synuclein plays an important role in the abnormal accumulation of aggregates seen in the neocortex, hippocampus and substantia nigra regions of the brain. With the understanding of this causative relationship, the search for potential therapeutic agents can be more closely directed toward the underlying overexpression of amyloidogenic proteins.

The following examples are intended to illustrate but not limit the present invention:

EXAMPLE 1

Ferric Iron Stimulates Aggregation of NACP/α-synuclein.

Figure 1B:
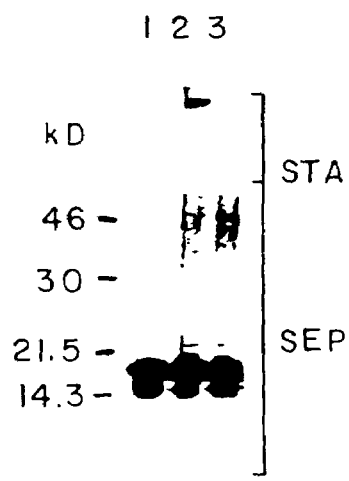
Figure 1C:
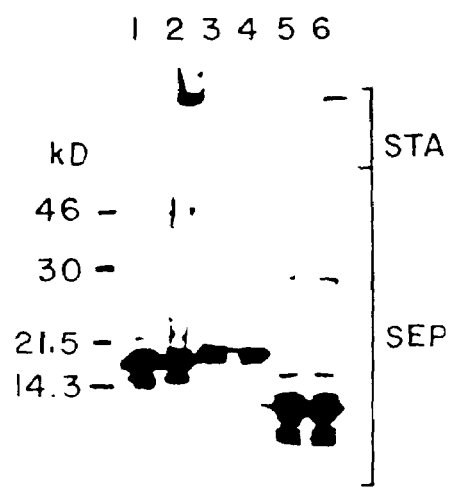

Results from immunoblotting analysis, shown in FIGS. 1a–c, indicate that ferric ion induced aggregation of human recombinant NACP/α-synuclein 140 after a 4 hour incubation period at pH 7.4 and 37° C. The aggregation of NACP/α-synuclein 140 proved to be dependent of the concentration of ferric ion in reaction, as can be observed in FIG. 1a where: lane 1=0 μM ferric ion, lane 2=1 μM ferric ion, lane 3=10 μM ferric ion, lane 4=100 μM ferric ion, lane 5=1 mM ferric ion, lane 6=100 μM ferric ion. NACP/α-synuclein was not included in lane 6. At a concentration of 1 μM of ferric ion, seen in lane 2, immuno-reactivity with NACP/α-synuclein 140 was observed at 55 kD. At 10 μM of ferric ion, some immuno-reactivity which failed to enter the gel matrix was noted, as can be seen in lane 3. Subsequently, at higher than 100 μM ferric ion, smears of the immunoreactive bands with retarded mobility became more remarkable and the intensity of the monomeric band at 18 kD was reduced, as can be seen in lanes 4 and 5. Although ferric ion is prone to forming ferric hydroxide, no immuno-reactivity was detectable in the samples which did not contain NACP/α-synuclein 140, as is evident in lane 6.

To confirm that ferric ion contributes to the retarded immuno-reactivity of NACP/α-synuclein 140, assay samples were treated with deferoxamine, a high affinity iron chelator. The results of the immunoblot analysis can be seen in FIG. 1b where lane 1=no treatment, lane 2=100 μM ferric ion, lane 3=100 μM ferric ion plus 10 mM deferoximine. In the assay sample treated with 10 mM deferoxamine, the immuno-reactivity, formally situated on the top of the gel, completely disappeared, as can be seen in lane 2, whereas the 55 kD result remained the same, indicating that chelation of ferric ion was partially effective in inhibiting aggregation of NACP/α-synuclein 140.

To determine the specificity of ferric ion to induce NACP/α-synuclein aggregation, both recombinant β-synuclein and NACP/α-synuclein 112 proteins were prepared and treated with ferric ion. As shown in FIG. 1c where lane 1=NACP/α-synuclein, lane 2=NACP/α-synuclein plus 100 μM ferric ion, lane 3=β-synuclein, lane 4=β-synuclein plus 100 μM ferric ion, lane 5=NACP/α-synuclein 112, lane 6=NACP/α-synuclein 112 plus 100 μM ferric ion. β-synuclein was not aggregated in lanes 3 and 4, whereas NACP/α-synuclein 112 was significantly aggregated in lanes 5 and 6. β-synuclein is a NACP/α-synuclein-related protein which possesses a highly conserved N-terminal region, a partially incomplete NAC domain in the mid region, and a non-homologous C-terminal region.

EXAMPLE 2

Aggregation of NACP/α-synuclein may be Associated with Iron-Catalyzed Oxidation.

Figure 2A:
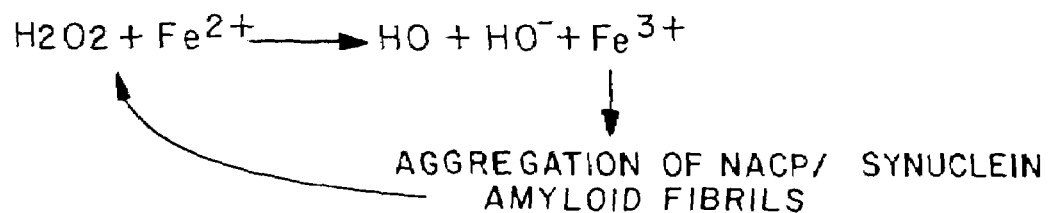
FIGS. 2a and 2b illustrate the mode for the possible link of NACP/α-synuclein aggregation to iron-catalyzed oxidative reaction, where
Figure 2B:
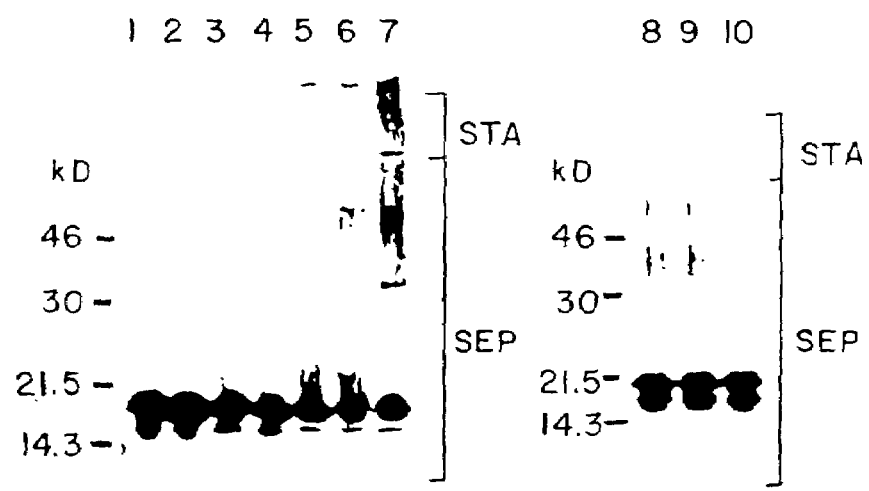

It was hypothesized that aggregation of NACP/α-synuclein might be linked to the iron-catalyzed oxidative reactions, represented in FIG. 2a, illustrating the hypothesis for the association of NACP/α-synuclein aggregation with iron-catalyzed oxidative reaction (Harber-Weiss reaction). In order to determine if an iron-catalyzed oxidative reaction promotes aggregation of NACP/α-synuclein, the human recombinant form of this molecule was incubated with ferrous ion (100 μM) and hydrogen peroxide. The combination resulted in a dose-dependent aggregation of NACP/α-synuclein, as can be seen in FIG. 2b which illustrates the immunoblotting analysis where NACP/α-synuclein (1 μM) is incubated with ferrous ion (100 μM) and increasing concentrations of $H_2O_2$: control (lane 1), 1 nM $H_2O_2$ (lane 2), 10 nM $H_2O_2$ (lane 3), 100 nM $H_2O_2$ (lane 4), 1 μM $H_2O_2$ (lane 5), 10 μM $H_2O_2$ (lane 6), 100 μM $H_2O_2$ (lane 7), control (lane 8), 10 μM $H_2O_2$ (lane 9), 100 μM $H_2O_2$ (lane 10). Ferrous ion was not included in lanes 8–10. The position of molecular weight markers (kD) are indicated on left). Bands representing retarded immuno-reactivity were observed in lane 7 when 100 μM hydrogen peroxide in the presence of ferrous ion was added. In contrast, no remarkable changes were observed when NACP/α-synuclein was incubated with hydrogen peroxide alone, shown in lanes 8–10. These results indicate that newly produced ferric ion, by Fenton reaction, may be responsible for the aggregation of NACP/α-synuclein. Other transition metals were also examined for their effect on NACP/α-synuclein aggregation. Cupric and manganese ions failed to induce the aggregation of NACP/α-synuclein in the presence of hydrogen peroxide, suggesting that the iron-catalyzed oxidative reaction may be a specific event in the aggregation of NACP/α-synuclein.

EXAMPLE 3

Aggregation of NACP/α-Synuclein Displays Amyloid-like Properties

In order to determine whether the ferric-ion induced in vitro aggregates of NACP/α-synuclein display amyloid-like characteristics, Thioflavine-S staining experiments were performed. A strong positive reactivity was obtained with NACP/α-synuclein 140 and NACP/α-synuclein 112, but not with β-synuclein, indicating the presence of ferric ion specifically induced the formation of amyloid-like fibrils of NACP/α-synuclein.

EXAMPLE 4

Production of Recombinant β-Synuclein and its Mutants in *E. coli*.

Figure 4:
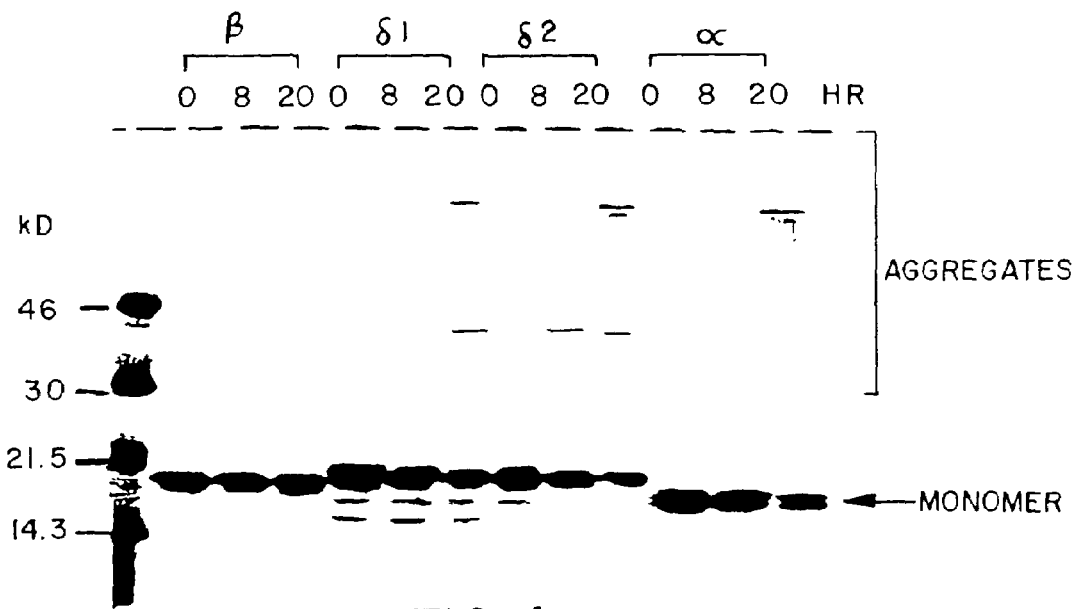
FIG. 4 illustrates aggregation of α-, and β-synuclein (and mutants) under high temperature conditions using SDS-PAGE analysis with a Coomassie brilliant blue stain.

As shown in FIG. 4, NACP/α-synuclein and β-synuclein share highly homologous N-terminal domains (shaded area), either a complete or an incomplete NAC domain (striped area), and less conserved C-terminal acidic domains (hatched area). β-synuclein lacks the middle portion of the NAC domain corresponding to amino-acids 73–83 of NACP/α-synuclein (GVTAVAQKTVE). β-synuclein δ1 was compensated for this portion. β-synuclein δ2 was further substituted with the N-terminal part of the NAC domain corresponding to amino-acids 63–72 of NACP/α-synuclein (ASHLGGAVFS to VTNVGGAVVT).

Figure 3:
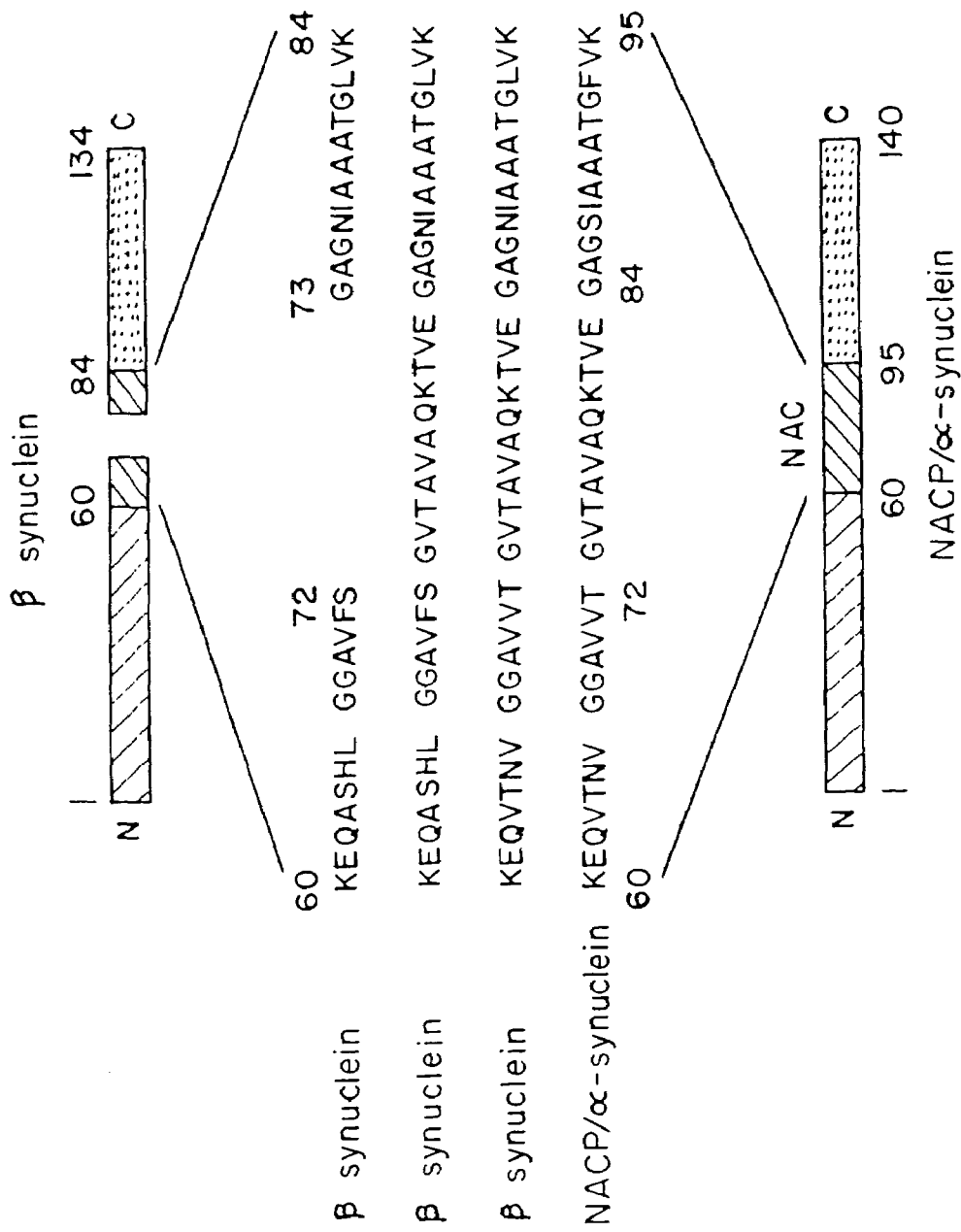
FIG. 3 is a schematic representation of β-synuclein (Seq ID 11), β-synuclein mutants (δ1 (Seq ID 12) and δ2 (Seq ID13)), and NACP/α-synuclein (Seq ID 14).

Human β-synuclein belongs to a synuclein family which includes NACP/α-synuclein and γ-synuclein. β-synuclein is highly homologous with NACP/α-synuclein, whereas, it has very little homology with γ-synuclein. NACP/α-synuclein and β-synuclein share highly conserved N-terminal regions, either a complete or an incomplete NAC domain in the middle portions, and a less conserved C-terminal acidic regions as can be observed in FIG. 3. Because NAC has already been shown to be a potent amyloidogenic peptide, it is believed that the incomplete NAC domain of β-synuclein may account for its lack of amyloidogenic properties.

Two mutants of β-synuclein were created by the site directed mutagenesis of β-synuclein cDNA as shown in FIG.

3. β-synuclein δ1 compensated for the deleted portion of the NAC domain corresponding to the amino-acids 72–83 of NACP/α-synuclein, whereas, β-synuclein δ2 was further substituted with the N-terminal portion of the NAC domain corresponding to amino-acids 63–72 of NACP/α-synuclein. Recombinant proteins were produced using a standard *E. coli* system and high purity products were generated using SDS-PAGE analysis, seen as FIG. 4. 20 μM each of β-synuclein (β), β-synuclein δ1 (61), β-synuclein 62 (62), and NACP/α-synuclein (α) were incubated under the pH 6.9 at 65° C. conditions for the indicated time. After SDS-PAGE, the gel was stained with Coomassie brilliant blue Although the calculated molecular weight of β-synuclein is less than that of NACP/α-synuclein, the result of the SDS-PAGE analysis shows that NACP/α-synuclein migrated through the gel at a rate faster than β-synuclein and its mutants δ1 and δ2.

EXAMPLE 5

β-synuclein Mutants Aggregate Under High Temperature Conditions

In an in vitro system to examine the aggregation of NACP/α-synuclein, human recombinant NACP/α-synuclein was preferentially aggregated under a variety of conditions, including low pH, extended lag time and high temperature. β-synuclein was incubated under similar conditions, however little aggregation was observed in the SDS-PAGE analysis. To determine whether the incomplete NAC domain in β-synuclein could be a contributing factor in the absence of amyloidogenic properties of β-synuclein, samples of the proteins NACP/α-synuclein, β-synuclein, β-synuclein δ1 and α-synuclein δ2 were incubated in 100 mM sodium acetate, pH 6.9, at 65° C. Under like conditions, the SDS-PAGE analysis, seen in FIG. 5 where 20 μM each of β-synuclein (δ2) and NACP/α-synuclein (α) were incubated under the pH 6.9 at 65° C. conditions for 20 hours in the presence of various concentrations of congo red. The positions of molecular weight markers are indicated on the left side (kD). shows that NACP/α-synuclein was preferentially aggregated to form amyloid-like fibrils as were both of the β-synuclein mutants. The wild type β-synuclein showed no aggregation under the varied conditions.

After 8 hours incubation, the bands corresponding to possible dimers became visible and, after 20 hours incubation, bands corresponding to dimers and higher smears in both the separating and stacking portions of the gels was observed. The kinetics of the aggregation of β-synuclein δ2 was reproducibly faster than that of β-synuclein β1, indicating that the stringency of the NAC sequence is critical for the aggregation of NACP/α-synuclein. An essentially similar tendency toward aggregation was observed in both β-synuclein δ1 and β-synuclein δ2 when these proteins were incubated under the pH 6.9 conditions at 37° C. for 7 days.

Figure 5:
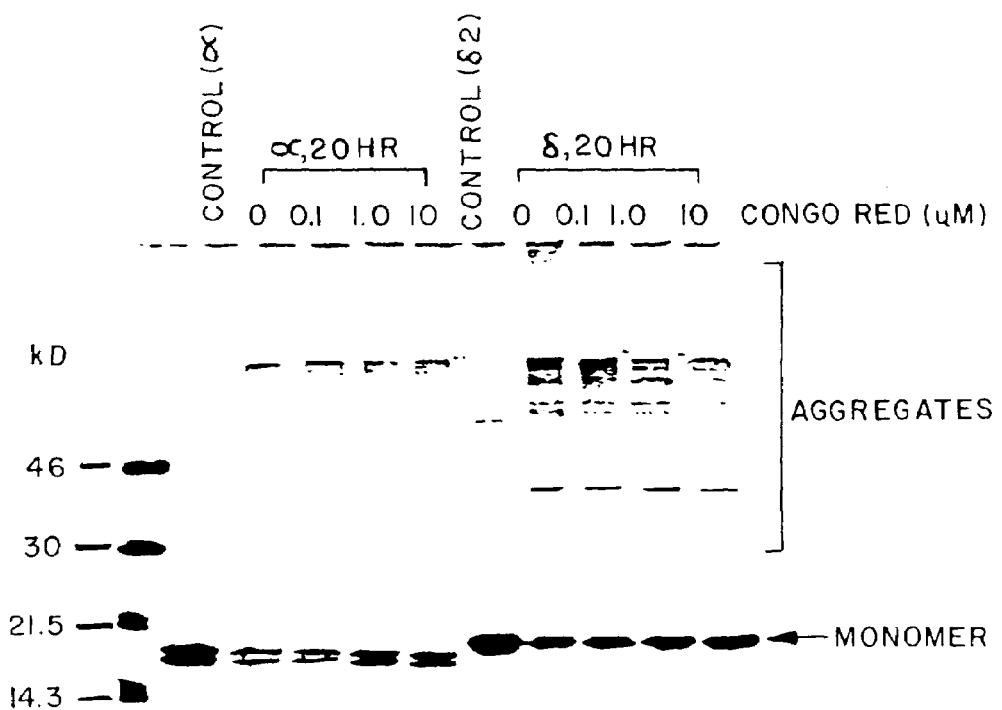
FIG. 5 illustrates results of immunoblot analysis showing inhibition of aggregation by congo red.

Since previous studies have shown that the aggregation of amyloidogenic proteins were to some extent inhibited by Congo red, increasing concentrations of Congo red were added in the present aggregation system. In both β-synuclein δ2 and NACP/α-synuclein, Congo red partly inhibited aggregation. As is shown in FIG. 5, the monomer bands were slightly but surely stabilized by treatment with micromolar concentrations of Congo red, which is consistent with other reported studies.

EXAMPLE 6

Aggregated β-Synuclein Mutants Display Amyloid-like Properties

To determine whether the β-synuclein mutants possess amyloid-like properties through the formation of aggregates, Thioflavine-S staining was performed. As previously reported, the aggregates of NACP/α-synuclein formed under the pH 6.9, 65 C conditions stained positive. Under similar conditions, the Thioflavine-S staining of β-synuclein had a negative result, whereas β-synuclein δ2 was clearly stained positive. This result is consistent with the previous SDS-PAGE analysis result, leading to the conclusion that the addition of the NAC domain to β-synuclein has the ability to transform that molecule into an amyloidogenic protein.

EXAMPLE 7

Binding of β-Synuclein to NACP/α-Synuclein

The interaction of NACP/α-synuclein with β-synuclein was assessed using a His-tagged pull down assay. NACP/α-synuclein was incubated with His-tagged β-synuclein, and was subsequently combined with $Ni^{2+}$ beads. The immobilized NACP/α-synuclein bound to the $Ni^{2+}$ beads was detected as a 18 kD monomer band by immunoblotting analysis using NACP/α-synuclein specific antibody, anti-NAC101–124. The results indicate that there is no specific binding of NACP/α-synuclein/$Ni^{2+}$ beads because there were no detectable bands in the absence of the His-tagged β-synuclein. Furthermore, the complex of NACP/α-synuclein and β-synuclein can be dissociated by boiling in the SDS sample buffer.

EXAMPLE 8

β-Synuclein Inhibits the Aggregation of α-Synuclein

The results from the His-tagged analysis led to the hypothesis that β-synuclein may modulate the aggregation of NACP/α-synuclein in vitro. To test this, β-synuclein was co-incubated with NACP/α-synuclein under the pH 6.9, 65° C. conditions. The effect of β-synuclein on the aggregation of NACP/α-synuclein was assessed by immunoblotting analysis using anti-NAC101–124.

According to the time-course results, NACP/α-synuclein was gradually aggregated. The 18 kD monomer bands were decreased while the soluble aggregates that represent oligomers in the separating gel and the insoluble aggregates detected in the stacking gel were increased. Co-incubation of an equimolar concentration of β-synuclein inhibited the aggregation of NACP/α-synuclein, however, an addition of IgG seemed not to have any inhibitory effect.

Figure 6A:
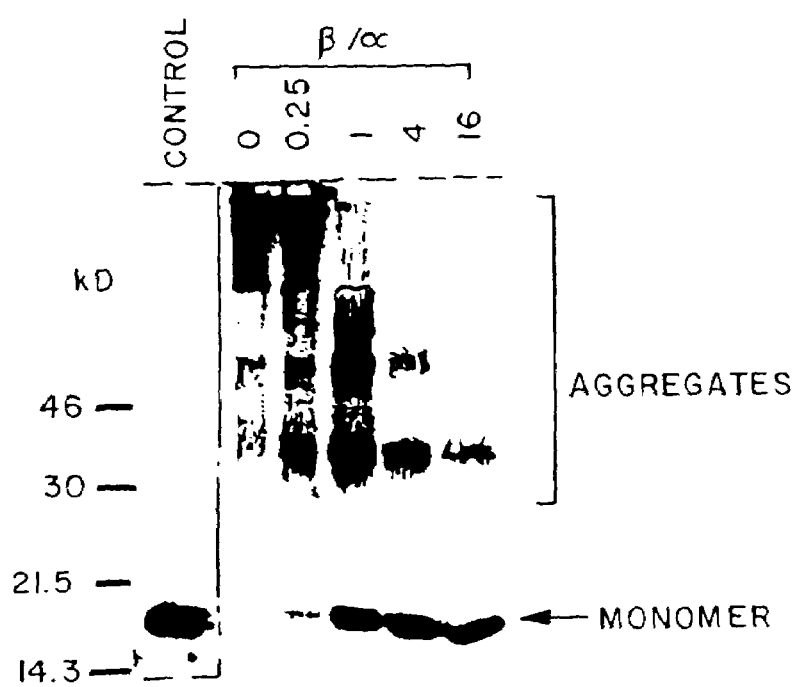
FIGS. 6a and 6b illustrates the results of analyses of the inhibitory effect of β-synuclein on the aggregation of NACP/α-synuclein, where the immunoblot analysis of FIG. 6a was performed using of anti-NACP/α-synuclein 102–114 antibody.
Figure 6B:
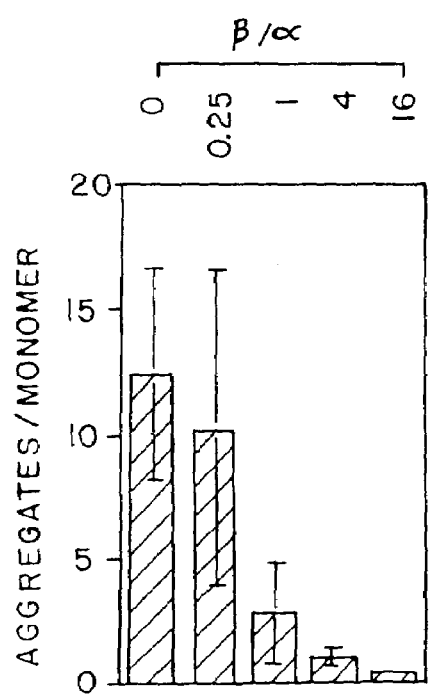

The dose-dependancy of β-synuclein in the inhibition of aggregation of NACP/α-synuclein was determined using proteins preparations at 20 hours incubation. As shown in FIG. 6a, 20 μM NACP/α-synuclein was incubated either alone, or in the presence of 20 μM of either β-synuclein or IgG under the pH 6.9 at 65° C. conditions for the indicated time. After SDS-PAGE, immunoblotting analysis was performed using anti-NACP/α-synuclein 102–114 antibody. The monomer and aggregates of NACP/α-synuclein are indicated on the right. β-synuclein significantly inhibited the aggregation of NACP/α-synuclein. Immuno-reactivities of the aggregates, which include both oligomers in the separating gel and the insoluble fractions within the stacking gel, and that of the 18 kD monomer were quantified. The relative ratio of aggregation versus the monomer was calculated for each sample and put in bar graph form as shown in Figure 6b. The ration of NACP/α-synuclein versus β-synuclein is shown on the top of the gels. The quantification of ratio of the aggregates versus the monomer was performed. Each bar represents the average +/− standard deviation (n=3). The results show that α-synuclein clearly suppresses the aggregation of NACP/α-synuclein, especially when there is an excess of β-synuclein in relation to NACP/α-synuclein.

EXAMPLE 9

Characterization of Transgenic NACP/α-Synuclein Mice

To assess whether abnormal accumulation of NACP/α-synuclein may contribute to the development of Lewy body disease, the neuronal overexpression of human α-synuclein directed by the PDGFβ promoter was investigated. Several lines of transgenic mice were created which overexpressed α-synuclein and then evaluated for neuronal alterations.

In the transgenic mice lines, 13 positive founders were identified and further bred for molecular and neuropathological characterization. A total of 121 mice were obtained from the F1, and of these, approximately 50% tested positive when evaluated by PCR. A subset of the positive mice from each line was sacrificed and the brain tissue was analyzed by ribonuclease protection assay, Western blot, and immunocytochemistry. These analyses identified at least four lines of mice that showed a consistent overexpression of NACP/α-synuclein at high, intermediate and low levels, the data for which are plotted in the representative autoradiograph of FIG. 7b showing α-synuclein mRNA levels in brain tissues from non-transgenic and transgenic mice and from humans with neurological disease. At the mRNA level, transgenic NACP/α-synuclein overexpression ranged from 0.25 to 3.0 fold over endogenous levels. The highest levels of the transgene message expression were found in the deeper layers of the neocortex, olfactory bulb, and pyramidal cell layer of the hippocampus. In contrast, the striatum, cerebellum, thalamus, substantia nigra and brainstem showed lower levels of transgene expression. In the neocortex, the highest levels of transgene expression were observed in layers 5 and 6 of the occipital, frontal and cingulate cortex. Endogenous murine NACP/α-synuclein had a similar distribution throughout the brain compared to human NACP/α-synuclein; however, within the neocortex, endogenous NACP/α-synuclein was evenly distributed in all layers. Both transgenic and endogenous levels of NACP/α-synuclein expression in the substantia nigra were low when compared to levels in the cortex.

Consistent with results from ribonuclease protection assays, Western blot analysis showed that the highest expressing transgenic line also displayed the highest levels of NACP/α-synuclein immunoreactivity, as shown in FIG. 7c, which is the PhosphorImager analysis of human α-synuclein mRNA expressed as a percentage of the human control. Immunocytochemical analysis showed that while, in the control line, NACP/α-synuclein immunoreactivity was mainly associated with presynaptic terminals, in the NACP/α-synuclein transgenic mouse line, extensive immunoreactivity was accumulated both in presynaptic terminals and neuronal cell bodies in the deeper layers of the neocortex and the hippocampal CA3 region. FIG. 7e shows the Western blot analysis showing affinity-purified human- and mouse-specific α-synuclein antibodies. FIG. 7f shows the PhosphorImager analysis of human α-synuclein signals from semi-quantitative Western blots of human α-synuclein expression in the different transgenic lines. The higher expression transgenic mice showed more extensive labeling in neuronal cell bodies and synapses compared to the lower expression transgenic mice. Doubling-labeling analysis confirmed that neurons in the neocortex and hippocampus that displayed high levels of NACP/α-synuclein mRNA expression also showed intense NACP/α-synuclein immunoreactivity. Mice from the four transgenic lines and the non-transgenic littermates were further bred for neuropathological analysis. A total of 6 in the D line (highest expressors), 6 in the A line (low expressors), 6 in the B line (low expressors), 6 in the C line (lowest expressors), 6 in the M line (intermediate expressors) of transgenes and 25 non-transgene mice were included for this study.

EXAMPLE 10

High Levels of Wild Type NACP/α-Synuclein Expression is Associated with Neuronal Alterations Immunocytochemical analysis with species-specific antibodies showed that the intraneuronal inclusions observed in the transgenic mice were exclusively labeled with the wild type human NACP/α-synuclein antibody, but not with the antibody recognizing the endogenous mouse form. These inclusions were more frequently seen in neurons in the deeper layers of the neocortex and in the CA3 region of the hippocampus. Confocal analysis revealed that in the high expression PDGF-NACP/α-synuclein line, abnormal accumulation of NACP/α-synuclein was accompanied by loss of presynaptic terminals in the neocortex as well as a loss of neurofilament expressing neurons in the neocortex and hippocampus. Compared to the non-transgene control littermates and the lower expression transgenic mice, high expression mice displayed intense ubiquitin immunoreactivity in neurons in the deeper layers of the neocortex and hippocampus. Double-immunolabeling studies showed that neurons displaying intense ubiquitin immunoreactivity also showed NACP/α-synuclein immunoreactivity in their cell bodies.

In order to further characterize the neuronal alterations in the higher expression transgenic mouse line, ultrastructural analysis was performed. In younger transgenic mice, ultrastructural analysis revealed the presence of small electrodense deposits associated with the RER and larger deposits with a dense core were observed in the nucleolis. In older transgenic mice, the larger electrodense cytoplasmic inclusions, resembling Lewy bodies, contained clear vacuoles and were composed of fine granular material. These alterations were not observed in age-matched lower expression transgenic lines or in the non-transgenic littermates. The neurons of the lower expression transgenic lines also showed the presence of abundant small clear vesicles, multivesicular bodies and clatrin coated pits.

To determine if the electrodense intracellular inclusions found in the transgenic mice also contained NACP/α-synuclein immunoreactivity, immunogold electron microscopic analysis was performed. This analysis showed that colloidal gold particles decorated the electrodense inclusions in the transgenic mice. Analysis of selected neuronal populations was carried out with antibodies against parvalbumin, calbindin and tyrosine hydroxylase. Within the neocortex and hippocampus, calbindin identified pyramidal neurons and interneurons, while parvalbumin immunolabeled only interneurons. In the basal ganglia, parvalbumin and calbindin identified subsets of inhibitory neuronal populations, while the antibody against tyrosine hydroxylase labeled the neurophil in the neocortex and basal ganglia, presumably corresponding to the terminal fields from projecting neurons from the substantia nigra. When compared to controls, transgenic mice did not show significant alterations. The antibody against tyrosine hydroxylase intensely labeled nigral neurons; however, this population was not significantly affected in the transgenic mice when compared to controls. It is unclear why no fibrillar structures were detected in association with the electrodense inclusions in the transgenic mice. It is possible that additional stress conditions, such as formation of free oxygen radicals, may be necessary to promote fibrillar aggregation of human α-synuclein.

Although the invention has been described with reference to the examples provided above, it should be understood that various modifications can be made without departing from the spirit of the invention. Accordingly, the invention is limited only by the following claims:

What is claimed is:

1. A method for identifying an inhibitor of Non-Aβ Component of amyloid Precursor (NACP)/α-synuclein aggregation comprising:

providing a test compound, a first sample and a second sample, wherein each sample comprises NACP/α-synuclein derived from the same source;

inducing NACP/α-synuclein aggregation in the first sample and second sample by subjecting them to an iron-catalyzed oxidative condition, wherein the condition is achieved by adding an amount of exogenous ferric ion or exogenous ferrous ion and hydrogen peroxide effective to aggregate NACP/α-synuclein;

exposing the first sample to the test compound;

measuring an aggregation level of NACP/α-synuclein in the first sample and the second sample; and comparing the aggregation level of NACP/α-synuclein in the first sample and with the aggregation level of the second sample, wherein less aggregation in the first sample is indicative that the test compound is an inhibitor of NACP/α-synuclein aggregation.

2. The method of claim 1, wherein the test compound comprises β-synuclein.

3. The method of claim 1, wherein the first sample comprises cells that express NACP/α-synuclein.

4. The method of claim 3, wherein the cells are neuronal cells.

5. The method of claim 4, wherein the neuronal cells comprise cells of the substantia nigra region of the brain.

6. The method of claim 1, wherein the iron-catalyzed oxidative condition comprises ferric iron.

7. The method of claim 1, wherein the iron-catalyzed oxidative condition comprises ferrous iron and hydrogen peroxide.

8. The method of claim 1, wherein the NACP/α-synuclein comprises a human recombinant NACP/α-synuclein.

* * * * *

SEQUENCE LISTING

<160> NUMBER OF SEQ ID NOS: 10

<210> SEQ ID NO 1
<211> LENGTH: 30
<212> TYPE: DNA
<213> ORGANISM: Homo sapiens

<400> SEQUENCE: 1
ggattccata tggacgtgtt catgaagggc                                      30

<210> SEQ ID NO 2
<211> LENGTH: 54
<212> TYPE: DNA
<213> ORGANISM: Homo sapiens

<400> SEQUENCE: 2
ctccactgtc ttctgggcta ctgctgtcac accagagaac acagctcctc ccag           54

<210> SEQ ID NO 3
<211> LENGTH: 55
<212> TYPE: DNA
<213> ORGANISM: Homo sapiens

<400> SEQUENCE: 3
ggtgtgacag cagtagccca gaagacagtg gaggggggcag ggaacatcgc agcag          55

<210> SEQ ID NO 4
<211> LENGTH: 34
<212> TYPE: DNA
<213> ORGANISM: Homo sapiens

<400> SEQUENCE: 4
agatcgcggc cgcttacgcc tctggctcat actc                                 34

<210> SEQ ID NO 5
<211> LENGTH: 54
<212> TYPE: DNA
<213> ORGANISM: Homo sapiens

<400> SEQUENCE: 5
cgtcaccact gctcctccaa catttgtcac ctgttccttg gttttttcag ccac           54

<210> SEQ ID NO 6
<211> LENGTH: 51
<212> TYPE: DNA
<213> ORGANISM: Homo sapiens

<400> SEQUENCE: 6
gtgacaaatg ttggaggagc agtggtgacg ggtgtgacag cagtagccca g              51

<210> SEQ ID NO 7
<211> LENGTH: 24

-continued

```
<212> TYPE: DNA
<213> ORGANISM: Mus musculus

<400> SEQUENCE: 7
ccagcggccg ctctagaact agtg                                           24

<210> SEQ ID NO 8
<211> LENGTH: 25
<212> TYPE: DNA
<213> ORGANISM: Mus musculus

<400> SEQUENCE: 8
ccagtcgacc ggtcatggct gcgcc                                          25

<210> SEQ ID NO 9
<211> LENGTH: 24
<212> TYPE: PRT
<213> ORGANISM: Mus musculus

<400> SEQUENCE: 9

Gly Lys Gly Glu Glu Gly Tyr Pro Asp Glu Gly Ile Leu Glu Asp Met
1               5                   10                  15

Pro Val Asp Pro Gly Ser Glu Ala
            20

<210> SEQ ID NO 10
<211> LENGTH: 141
<212> TYPE: PRT
<213> ORGANISM: Mus musculus

<400> SEQUENCE: 10

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Thr Thr Lys Glu Gln Val Thr
    50                  55                  60

Asn Val Gly Gly Ala Val Val Thr Gly Val Thr Ala Val Ala Gln Lys
65                  70                  75                  80

Thr Glu Val Gly Ala Gly Asn Ile Ala Ala Thr Gly Phe Val Lys
                85                  90                  95

Lys Asp Gln Met Gly Lys Gly Glu Glu Gly Tyr Pro Gln Glu Gly Ile
                100                 105                 110

Leu Glu Asp Met Pro Val Asp Pro Gly Ser Glu Ala Tyr Glu Met Pro
            115                 120                 125

Ser Glu Glu Gly Tyr Gln Asp Tyr Glu Pro Glu Ala
        130                 135                 140
```